United States Patent [19]

Lonsinger et al.

[11] 4,389,350

[45] Jun. 21, 1983

[54] PREPARATION OF O,S-DIALKYL PHOSPHOROAMIDOTHIOATES

[75] Inventors: Jack J. Lonsinger, Liberty; Chester W. Halbleib, Holt, both of Mo.

[73] Assignee: Mobay Chemical Corporation, Kansas City, Mo.

[21] Appl. No.: 265,046

[22] Filed: May 19, 1981

[51] Int. Cl.³ .............................................. C07F 9/24
[52] U.S. Cl. ..................................... 260/989; 260/959
[58] Field of Search ................................ 260/989, 959

[56] References Cited

U.S. PATENT DOCUMENTS 3,639,547  2/1972  Magee ................................. 260/989

Primary Examiner—Anton H. Sutto
Attorney, Agent, or Firm—Sprung, Horn, Kramer & Woods

[57] ABSTRACT

In the isomerization of an O,O-dialkyl phosphoroamidothioate to an O,S-dialkyl phosphoroamidothioate by heating the O,O-dialkyl starting material in the presence of a catalyst, followed by recovery of the desired O,S-dialkyl end product, the improvement which comprises arresting the heating when about 40 to 70% of the O,O-dialkyl starting material has isomerized to O,S-dialkyl product, separating unreacted O,O-dialkyl starting material from the O,S-dialkyl isomerization product, and further treating the O,O-dialkyl starting material to effect further isomerization. The separation is effected either by cooling to crystallize out O,S-dialkyl isomer or by evaporating off the O,O-dialkyl starting material.

9 Claims, No Drawings

PREPARATION OF O,S-DIALKYL PHOSPHOROAMIDOTHIOATES

The present invention relates to an improvement in the known process for isomerizing O,O-dialkyl phosphoroamidothioates to O,S-dialkyl phosphoroamidothioates.

U.S. Pat. No. 3,639,547 describes the catalytic isomerization of O,O-dialkyl phosphoroamidothioates to O,S-dialkyl phosphoroamidothioates in accordance with the following equation:

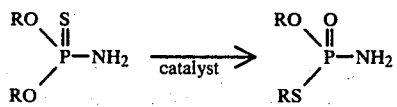

wherein R is an alkyl radical such as lower alkyl, especially methyl. Suitable catalysts include a methyl ester of an organic alkyl or carbocyclic aryl sulfonic acid in which the alkyl group is of 1 to 6 carbon atoms and the carbocyclic aryl group is of 6 to 10 carbon atoms, and especially dimethyl sulphate. While the catalyst may be employed in about 1 to 10 mol percent, especially 3 to 5 mol percent, the preferred amount is 4 mol percent with dimethyl sulphate and still higher with other catalysts. The reaction is exothermic and the temperature can be maintained at about 20° to 80° C. by cooling or heating, although it is preferably about 50° to 80° C.

While the process is generally satisfactory, the yields are at most about 75% with a portion of the balance of the product constituting unisomerized starting material and various by-products.

It is accordingly an object of the invention to improve such process by increasing the yield and/or decreasing the amount of catalyst required.

These and other objects and advantages are realized in accordance with the present invention pursuant to which the catalytic isomerization is arrested when about 40 to 70% of the O,O-dialkyl starting material has isomerized to O,S-dialkyl product. Thereafter the process involves separating the isomerization mass into catalyst and/or unreacted O,O-dialkyl starting material and into O,S-dialkyl isomerization product, and further treating the mixture of catalyst and O,O-dialkyl starting material to effect further isomerization.

As a result of the arrest and separation the overall yield of isomerization product is increased to about 85% or more and the product is of high purity. In addition it is possible to achieve these results while even reducing the amount of catalyst required.

The heating is generally effected at about 40° to 70° C. and preferably about 55° to 60° C. The duration of the initial heating generally is from about 0.5 to 1 hour, depending on the temperature, they being interrelated so as to effect the 40 to 70% isomerization, preferably about 55 to 60% isomerization.

The catalyst can be any of those conventionally employed and the amount present can also be conventional although it is possible to achieve the instant advantages even with as little as 2.5% and even 1% based on the weight of the O,O-dialkyl ester.

Following arrest of heating the isomerization mass can be subjected to either of two different treatments. In one, the mass is cooled to a temperature below about room temperature, preferably about 0° C. or even lower, whereupon the O,S-diallyl isomer crystallizes out selectively. The residence time for crystallization may be as short as 30 minutes although for substantial recovery of all the O,S-dialkyl isomer 6 hours has proven desirable. The crystals, which are then separated from the mother liquor as by fitration or centrifugation, have a purity in excess of about 95% and even as high as about 98%.

Upon reheating, the mother liquor comprising starting material and catalyst and some by-product undergoes isomerization. In this stage the mass is heated at the same temperatures as before, preferably for at least 30 minutes, until less than about 10% of the original O,O-dialkyl ester is left unisomerized. There is obtained an additional batch of O,S-dialkyl isomer of essentially the same composition as in the conventional process which can be purified, if desired. The overall yield of O,S-dialkyl isomer is about 85% or greater. It is even possible to repeat the isomerization interruption and crystal removal a second time prior to final isomerization.

In the alternate way of processing the mass when heating is arrested, the mass is subjected to distillation e.g. thin film evaporation at about 150° C. and 1–2 mm Hg, to boil off unreacted O,O-dialkyl starting material which is then used as part of the feed for another cycle. The distillation residue is O,S-dialkyl phosphoroamidothioate in a purity of about 85–95%. Overall the net yield is about 90% or greater.

The processes can be effected batchwise or continuously.

The invention is illustrated in the following examples:

EXAMPLE 1

O,O-Dialkyl phosphoroamidothioate was supplied to an isomerizer at the rate of 182 grams/minute along with dimethyl sulphate at the rate of 7.5 grams/minute. The isomerizer was held at 60° C. and, after an average residence time of 25 minutes, material was continuously passed to a crystallizer maintained at about 9° C. with a residence time of 45 minutes. Material from the crystallizer was continuously centrifuged yielding 66.1 grams per minute of O,S-dialkyl crystals assaying 94.3% O,S-dialkyl and 4.4% O,O-dialkyl. After 24 hours of operation this corresponded to a feed of 576.4 pounds of O,O-dialkyl starting material and a recovery of 201.1 pounds of O,S-dialkyl product.

383.3 Pounds of the centrifuged liquid, assaying 54.6% O,O-dialkyl and 26.4% O,S-dialkyl, plus catalyst and by-product were then collected and batchwise isomerized at 60° C. for 60 minutes, and then cooled to yield 372.8 pounds of product assaying 70.3% O,S-dialkyl and 11% O,O-dialkyl for an overall yield of 85.6%.

EXAMPLE 2

A feed stream of O,O-dialkyl phosphoroamidothioate, half fresh and half recycle, was supplied to a steel tube at the rate of 0.333 pounds per minute along with dimethyl sulphate at the rate of 1.71 ml per minute, coming to 1.5% dimethyl sulphate. The tube was coiled in a bath maintained at 60° C. the liquid having a 1 hour residence time in the tube. The material then passed to a thin film evaporator at 150° C. and 2 mm Hg where 50% of the feed was taken off as distillate and recycled. The balance was cooled to 45° C. and comprises 88% O,S-dialkyl isomer for an overall yield of 90%.

It will be understood that the specification and examples are illustrative but not limitative of the present invention and that other embodiments within the spirit and scope of the invention will suggest themselves to those skilled in the art.

We claim:

1. In the isomerization of an O,O-dialkyl phosphoroamidothioate to an O,S-dialkylphosphoroamidothioate by heating the O,O-dialkyl starting material in the presence of a catalyst, followed by recovery of the desired O,S-dialkyl end product, the improvement which comprises arresting the heating when about 40 to 70% of the O,O-dialkyl starting material has isomerized to O,S-dialkyl product, separating unreacted O,O-dialkyl starting material from O,S-dialkyl isomerization product, and further treating the O,O-dialkyl starting material to effect further isomerization.

2. A process according to claim 1, wherein heating is arrested after about 55 to 60% of the O,O-dialkyl starting material has undergone isomerization.

3. A process according to claim 2, wherein the starting material is O,O-dimethyl phosphoroamidothioate, and the initial heating and the continued heating are effected at about 40° to 70° C.

4. A process according to claim 1, wherein separation is effected by cooling to a temperature below about room temperature and permitting the mass to stand at such temperature thereby to crystallize out the desired O,S-dialkyl product, and separating the crystalline material from the liquid.

5. A process according to claim 4, wherein the initial heating and the further treatment are effected at about 40° to 70° C., and cooling is effected to below about 0° C.

6. A process according to claim 1, wherein separation is effected by distilling off about 40 to 60% of the mass.

7. A process according to claim 6, wherein the distillate is recycled for use as part of the initial feed in another cycle of isomerization.

8. A process according to claim 7, wherein the initial heating and the subsequent cycle to effect isomerization are effected at about 40° to 70° C., and distillation is effected at a higher temperature.

9. A process according to claim 6, wherein the catalyst is employed in about 1 to 2.5% by weight of the feed.

* * * * *